June 22, 1976 C. OTT Plant Pat. 3,916
YELLOW CHRYSANTHEMUM
Filed March 6, 1975
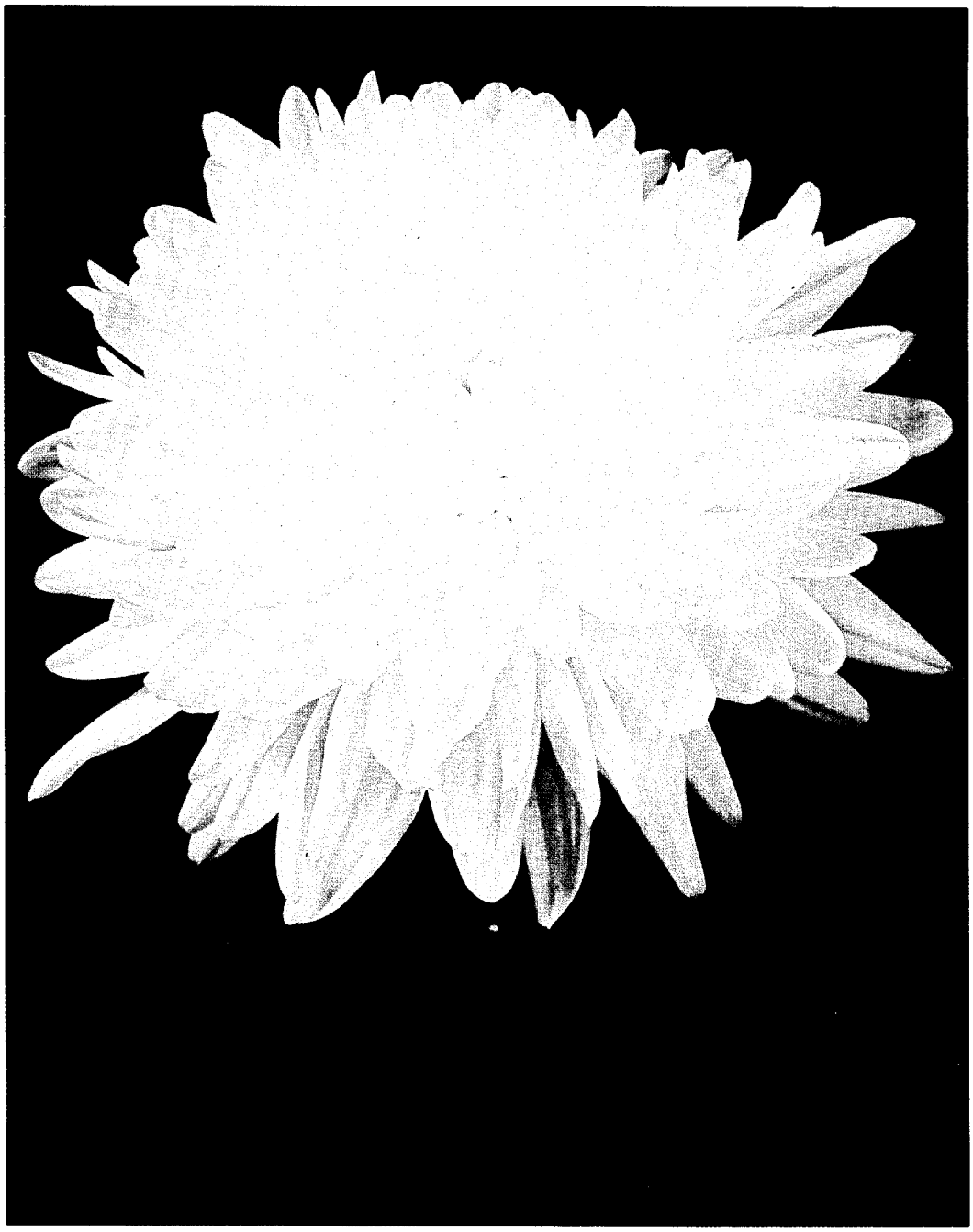

United States Patent

Plant Pat. 3,916
Patented June 22, 1976

3,916
YELLOW CHRYSANTHEMUM

Cleveland Ott, 677 Grater Ave., Graterford, Pa. 19426

Filed Mar. 6, 1975, Ser. No. 555,975
Int. Cl. A01h *5/00*
U.S. Cl. Plt.—78 1 Claim

ABSTRACT OF THE DISCLOSURE

A new and distinct variety of yellow chrysanthemum is disclosed, which is characterized particularly by a bloom of a much deeper yellow color, petals which maintain an incurving configuration for the entire blossoming period, and which bloom three days later than the parent Yellow Paragon.

*Origin of the Variety*

This variety of yellow chrysanthemum was discovered by the applicant as a sport in a nursery bed of Yellow Paragon (P.P. 3,405) chrysanthemums in applicant's heated greenhouse near Graterford in Eastern Pennsylvania. This discovery was made in the latter part of October 1974.

*Asexual Reproduction of the Variety*

Subsequent to applicant's discovery of this new and distinct variety of yellow chrysanthemum, applicant asexually reproduced this new and distinct variety in his heated greenhouse by separately planting and cultivating this new and distinct sport. The asexually reproduced chrysanthemums have uniform new and distinct characteristics.

*Summary of the Variety*

This new and distinct variety of yellow chrysanthemum is characterized by three new and distinct features:

(1) A much deeper yellow color than the parent Yellow Paragon chrysanthemum; the color of the new chrysanthemum is designated on the Royal Horticultural Society (R.H.S.) color chart as "6A" whereas the color of the parent is designated "6C"; the color of the new flower is designated on the Horticultural Color Chart (H.C.C.) as "Sulphur Yellow HCC1" whereas the color of the parent is designated "Sulphur Yellow HCC½"; the color of the new flower is designated on the British Colour Council (B.C.C.) Dictionary of Colour Standards as "Sulphur BCC 112" whereas the color of the parent has no designation on the B.C.C. Colour chart;

(2) Petals which maintain an incurving (decorative) form with a higher crown during the entire blooming period, rather than having an outcurving characteristic partway through the blooming period as is usually found in Yellow Paragon chrysanthemums; and (3) Blossoms that appear three days later than encountered with the parent Yellow Paragon chrysanthemum.

*Brief Description of the Drawing*

The drawing is an illustration, by photographic reproduction in color, of the new and distinct yellow chrysanthemum of this application.

*Detailed Description of the Variety*

The new and distinct variety of yellow chrysanthemum of this application was asexually reproduced from a sport of the parent Yellow Paragon chrysanthemum.

The blossoms of this new and distinct variety of yellow chrysanthemum has a much deeper yellow color than is seen in the parent Yellow Paragon chrysanthemum.

The new and distinct vareity of yellow chrysanthemum of the present application has the characteristic of the petals of the blossom maintaining an incurving form throughout the blooming period, which is contrary to normal Yellow Paragon chrysanthemums. Normal Yellow Paragon chrysanthemums partway through the blooming period tend to curve downward, assuming an outcurving form, as if they were dying, while actually they are not, thereby thus diminishing the beatuy of the flower. The present new and distinct variety of yellow chrysanthemum maintains its petals in an incurving appearance throughout the entire blooming period, a characteristic normally only found in chrysanthemums such as the White Paragon.

The present new and distinct variety of yellow chrysanthemum blooms three days later than normal yellow chrysanthemums such as the Yellow Paragon.

Otherwise, the new and distinct variety of yellow chrysanthemum of this application has characteristics quite similar to the Yellow Paragon chrysanthemum plant and flower.

What is claimed is:

1. A new and distinct variety of yellow chrysanthemum, substantially as illustrated and described, characterized particularly by: a deeper hue of yellow color in the blossom relative to the parent Yellow Paragon chrysanthemum; petals of the blossom which maintain an incurving form during the entire flowering period; and a bloom which appears three days later than the parent Yellow Paragon chrysanthemum.

No reference cited.

ROBERT E. BAGWILL, Primary Examiner